(12) United States Patent
Frankel

(10) Patent No.: US 7,912,578 B1
(45) Date of Patent: *Mar. 22, 2011

(54) SYSTEM AND METHOD FOR CONVEYING PHARMACEUTICALS FROM AN AUTOMATED MACHINE

(76) Inventor: Mark E. Frankel, Lower Gwynedd, PA (US)

( * ) Notice: Subject to any disclaimer, the term of this patent is extended or adjusted under 35 U.S.C. 154(b) by 568 days.

This patent is subject to a terminal disclaimer.

(21) Appl. No.: 11/820,564

(22) Filed: Jun. 21, 2007

Related U.S. Application Data

(63) Continuation-in-part of application No. 11/476,220, filed on Jun. 27, 2006, now Pat. No. 7,483,766.

(51) Int. Cl.
*G06F 17/00* (2006.01)
(52) U.S. Cl. ......... 700/237; 700/236; 700/240; 700/241
(58) Field of Classification Search .................. 700/236, 700/237, 240, 249
See application file for complete search history.

(56) References Cited

U.S. PATENT DOCUMENTS

| | | | |
|---|---|---|---|
| 5,797,515 A | 8/1998 | Liff et al. ........................ 221/2 |
| 5,883,370 A | 3/1999 | Walker et al. ................. 235/375 |
| 6,067,524 A | 5/2000 | Byerly et al. .................... 705/3 |
| 6,330,491 B1 * | 12/2001 | Lion ............................. 700/237 |
| 6,529,801 B1 * | 3/2003 | Rosenblum ................... 700/237 |
| 7,123,989 B2 * | 10/2006 | Pinney et al. ................. 700/237 |
| 7,194,333 B2 * | 3/2007 | Shoenfeld ..................... 700/236 |
| 7,483,766 B1 * | 1/2009 | Frankel ......................... 700/240 |

* cited by examiner

*Primary Examiner* — Timothy R Waggoner
(74) *Attorney, Agent, or Firm* — LaMorte & Associates

(57) ABSTRACT

A system and method for conveying regulated pharmaceuticals to a patient in an automated manner. A database is provided that contains information on patients and the prescriptions prescribed to those patients. An automated conveying machine is supplied that contains an inventory of prepackaged pharmaceuticals that can be independently vended. An interface is provided proximate the automated conveying machine. Prescription data is entered into the interface. The prescription data identifies a specific patient and a specific prepackaged pharmaceutical. The prescription data is compared to information in the database for confirmation. The automated conveying machine receives a confirmation signal if the prescription data is valid. If the requested prepackaged pharmaceutical is present within the inventory of said automated conveying machine and the confirmation signal has been received, then the automated conveying machine is activated. Inventory controls are present that prevent the system from overselling.

9 Claims, 4 Drawing Sheets

SYSTEM AND METHOD FOR CONVEYING PHARMACEUTICALS FROM AN AUTOMATED MACHINE

RELATED APPLICATIONS

This application is a continuation-in-part of U.S. patent application Ser. No. 11/476,220, entitled System And Method For Prescribing And Conveying Pharmaceuticals Within The Premises Of A Healthcare Provider, filed Jun. 27, 2006 now U.S. Pat. No. 7,483,766.

BACKGROUND OF THE INVENTION

1. Field of the Invention

In general, the present invention relates to systems and methods that are used to convey pharmaceuticals in an automated manner. More particularly, the present invention relates to the operating systems that govern the operation of automated machines that hold prescription pharmaceuticals.

2. Prior Art Description

When a person is sick, they commonly use the services of a professional healthcare provider. In the standard course of operation, healthcare providers regularly examine and diagnose patients in their offices. Typically, a sick patient will meet with the healthcare provider in his/her office. The healthcare provider will diagnose the illness and suggest a course of action to treat the illness. Often, the suggested course of action involves taking medication. If the selected medication is a controlled pharmaceutical, the healthcare provider writes a prescription for the patient. The patient takes the prescription to a pharmacy, wherein a pharmacist fills the prescription. As such, sick patients must proceed through a two-step process before they receive medication for their ailment. The patient must first visit with a healthcare provider to obtain a prescription. The patient must then visit with a pharmacist to have the prescription filled.

The two-step process of obtaining medication for an ailment presents many problems for a patient. The obvious problem is one of inconvenience. It takes time to visit both a physician's office and a pharmacy. It also takes time for a pharmacy to fill a prescription. Consequently, there can be a delay of many hours between when a physician hands a patient a prescription for a medication and the time that the patient has that medication in hand.

Furthermore, just because a patient is given a prescription does not mean that the patient will fill the prescription. A patient may believe that the physician is wrong in their diagnosis. Alternatively, a patient may procrastinate, hoping the ailment will pass without medication. A patient may also lose the prescription, forget about the prescription or purposely not fill the prescription for a variety of financial, religious and/or personal reasons.

The other problems associated with the two-step process of receiving medications are much less obvious, but far more important. When a patient arrives at a pharmacy, the patient must hand the pharmacist the prescription. The pharmacist must assume that the prescription is proper for both the patient and the illness being treated. In other words, the pharmacist must assume that the doctor did not make any error in writing the prescription and has handed the correct prescription to the correct patient. The pharmacist must then decipher the physician's handwriting and understand what has been prescribed and in what dosage. If the pharmacist misreads the prescription in any way, the prescription will be incorrectly filled.

Assuming the physician did not err in issuing the prescription and the pharmacist did not err in reading the prescription, the pharmacist must then properly fill the prescription and label the prescription. If the pharmacist errs in either filling or labeling the prescription, the patient may take the wrong medication or may take the right medication, but the wrong dosage. The patient may also be given the proper medication, in the proper dosage, but with incorrect dosing instructions.

Finally, once a prescription is prepared and labeled, it must be given to the correct patient. Most pharmacies do not ask to see identification from patients. The prescription is often just handed to the person who asks for the prescription and pays for the prescription.

Most patients assume that the prescription given to them at the pharmacy is correct. If a patient is handed the wrong prescription, there is a good chance that the patient will take that medication without ever reading the label on the bottle.

In addition to all the problems that may accidentally occur in traditional systems, many people also attempt fraudulently to acquire pharmaceutical prescriptions. Such people take advantage of the many problems of the system to forge, falsify, and steal pharmaceuticals.

It will therefore be understood that in order for a person to properly receive a prescription, there must be no human error in writing, handling, filling, labeling and delivering the prescription. Although the system works correctly the vast majority of the time, human error is always present. Thousands of such errors occur every year. These errors could result, either directly or indirectly, in deaths, permanent injury, illness, harmful drug interactions and untreated disease. This creates liabilities to pharmacists and doctors resulting in increased healthcare costs for everyone.

Despite training and safety protocols, the only way to reduce human error is to minimize the points in the system where human error can occur. To prevent physicians from writing illegible prescriptions, many electronic prescription systems have been created that electronically transmit prescriptions to pharmacies. Such prior art systems are exemplified by U.S. Pat. No. 6,067,524 to Byerly, entitled Method And System For Automatically Generating Advisory Information For Pharmacy Patients Along With Normally Transmitted Data; and U.S. Pat. No. 5,883,370 to Walker, entitled Automated Method For Filling Drug Prescriptions.

Perhaps the most common place where errors occur is in the filling, labeling and delivery of the prescription by the pharmacist. One way to minimize human error in these processes is to create automated machines that convey prepackaged pharmaceuticals.

There are many ways to convey prepackaged goods to the public using automation. The most common way to convey prepackaged goods is through the use of vending machines. Vending machines can vend any product that is placed into the vending machines, including prepackaged pharmaceuticals. Vending machines can also be left accessible to the public at all times, thereby enabling a person to fill a prescription at their own convenience. Vending machines specifically configured to vend prescription pharmaceuticals are exemplified by U.S. Pat. No. 5,797,515, to Liff, entitled Method For Controlling A Drug Dispensing System.

Replacing a human pharmacist with an automated vending machine presents its own set of problems. First, the vending machine must be manually filled with the proper medications. Human error may cause the vending machine to be incorrectly filled. Furthermore, as most everyone has experienced, vending machines do not always vend properly. Merchandise gets jammed. Sometimes nothing vends from the machine, sometimes two products accidentally vend from the machine.

A need therefore exists for an improved automated conveying system for prescription pharmaceuticals that safeguards against many common errors that are inherent in prior art automated systems. This need is met by the present invention as described and claimed below.

SUMMARY OF THE INVENTION

The present invention is a system and method for conveying regulated pharmaceuticals to a patient in an automated manner. A database is provided that contains information on patients and the prescriptions prescribed to those patients. An automated conveying machine is supplied that contains an inventory of prepackaged pharmaceuticals that can be independently vended.

An interface is provided proximate the automated conveying machine. Prescription data is entered into the interface. The prescription data identifies a specific patient and a specific prepackaged pharmaceutical. The prescription data is compared to information in the database for confirmation. The automated conveying machine receives a confirmation signal if the prescription data is valid.

If the requested prepackaged pharmaceutical is present within the inventory of said automated conveying machine and the confirmation signal has been received, then the automated conveying machine is activated.

Inventory controls are present that prevent the system from overselling.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system and method can be used to convey controlled materials other than pharmaceuticals, the present invention is particularly well suited for use in prescribing and conveying prescription pharmaceuticals. Accordingly, the present invention system and method is described for use in conveying prescription pharmaceuticals in order to set forth the best mode contemplated for the invention.

Figure 1:
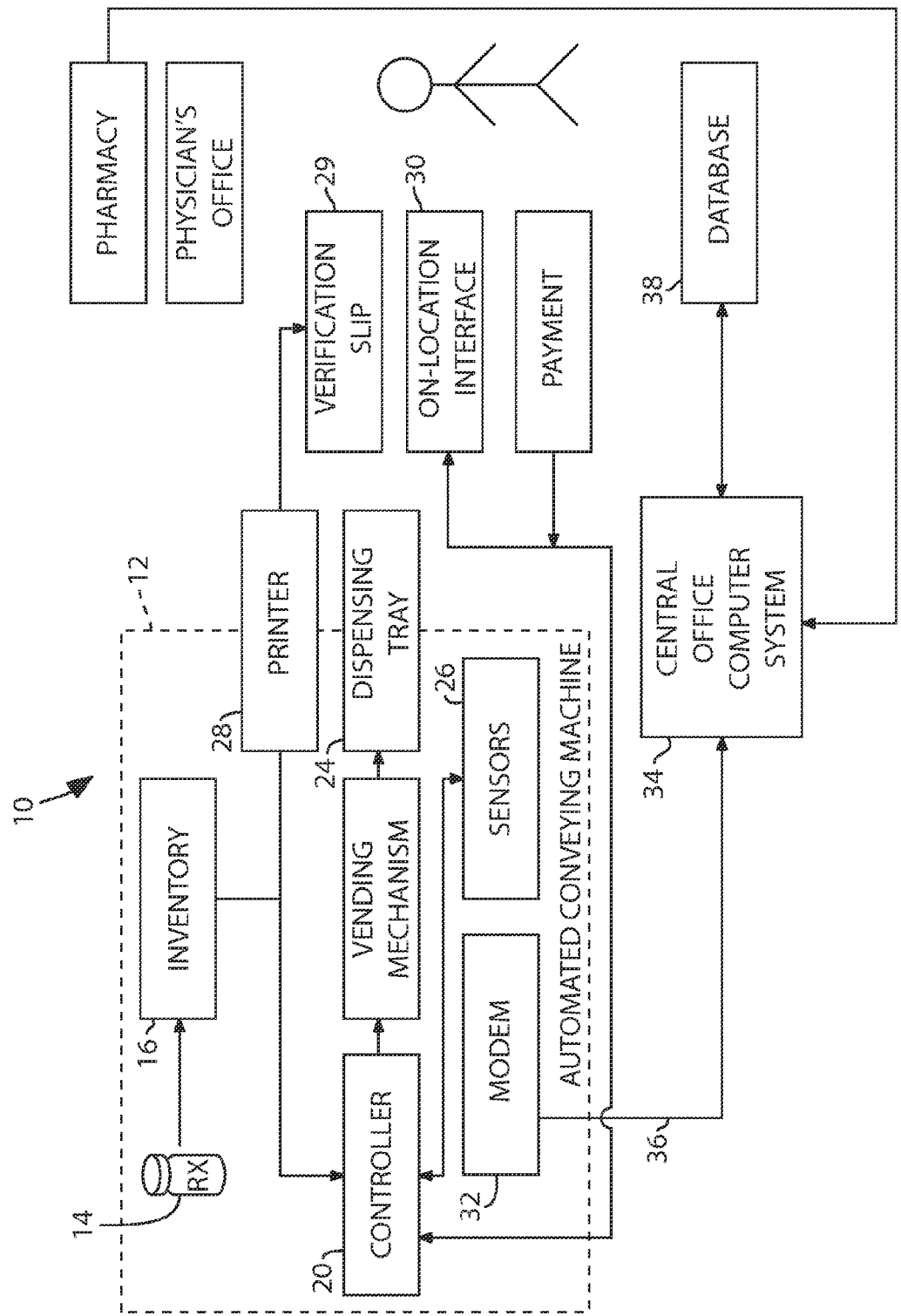
FIG. 1 is an exemplary schematic of the present invention system.

Referring to FIG. 1, a schematic of the present invention system 10 is shown. The present invention system 10 utilizes a custom automated conveying machine 12 that stores and conveys prepackaged units-of-use 14. For the purposes of this description, a unit-of-use is a bottle, jar, vial, tube, syringe, package or other receptacle that is prefilled with pharmaceutical in a volume large enough to complete a course of treatment. The automated conveying machine 12 is preferably kept in a semi-private location, such as in a physician's office or in a pharmacy. However, the automated conveying machine 12 may be present in public areas for direct access by patients.

The automated conveying machine 12 contains a stocked inventory 16 of prepackaged units-of-use 14. The prepackaged units-of-use 14 that are kept in the automated conveying machine 12 depend upon the perceived needs of the community of patients. For instance, if the automated conveying machine 12 were located in a pediatric physician's office, the automated conveying machine 12 might, among other things, contain various antibiotics in dosages suitable for children of different weights and ages. If located in a geriatric physician's office, the automated conveying machine 12 might contain, among other things, prepackaged units-of-use 14 for arthritis and hypertension. It will therefore be understood that the automated conveying machine 12 is stocked with the prepackaged units-of-use 14 that are most typically prescribed by the perceived community of patients.

The automated conveying machine 12 contains a controller 20 that governs the various electro-mechanical functions of the automated conveying machine 12. The automated conveying machine 12 contains a vending mechanism that physically moves a selected unit-of-use 14 from the inventory 16 to a dispensing tray 24. It is only after a unit-of-use 14 is in the dispensing tray 24 that it can be removed from the automated conveying machine 12.

Sensors 26 are provided within the automated conveying machine 12. The sensors 26 detect whether or not a unit-of-use 14 has properly moved from the inventory 16 to the dispensing tray 24. The information gathered by the sensors 26 is read by the controller 20.

A printer 28 is provided that is coupled to the controller 20. The printer 28 can be a tabletop printer 28. However, in the shown embodiment, the printer 28 is contained within the structure of the automated conveying machine 12. The printer 28 produces a verification slip 29, the purposes of which will be later described.

To activate the automated conveying machine 12, a user must interact with an on-location interface 30. If the automated conveying machine 12 is in a physician's office, the on-location interface 30 can be a computer terminal used by the professional staff. If the automated conveying machine 12 is in a pharmacy, the on-location interface 30 can be a computer terminal located behind the pharmacist's counter. If in a remote location, the on-location interface 30 can be a panel located on the front of the automated conveying machine 12 for direct use by the patient.

Regardless of where the on-location interface 30 is located, the on-location interface 30 is used for three primary purposes. As will later be described in more detail, those purposes include identifying the patient, selecting the unit-of-use 14 prescribed to the patient, and acknowledging payment.

Identifying the patient can be achieved by simple data entry of the patient's name or another identifier, such as social security number. The on-location interface 30 may optionally include a biomedical scanner, such as a fingerprint reader, if user identification requires authentication.

The selection of the unit-of-use 14 is preferably performed using a menu select system that displays available choices contained within the inventory 16 of the automated conveying machine 12.

Payment for the unit-of use 14 can be achieved in different ways. If the automated conveying machine 12 is located in a pharmacy or in a physician's office, then payment can be made to the office personnel. The payment can be entered into the system through the on-location interface 30. If the automated conveying machine 12 is located at a remote location, a payment means is provided within the on-location interface 30. The payment means can be a credit card reader and/or cash verification mechanism, such as those used on traditional vending machines.

Since the automated conveying machine 12 contains controlled substances, the automated conveying machine 12 will not operate unless it receives an authorization signal that indicates that the patient requesting a unit-of-use 14 is legally entitled to possess that unit-of-use 14. The authorization signal can be entered in two ways. If the automated conveying machine 12 is located in a pharmacy or in a physician's office, the authorization signal can be entered by the professional staff via the on-location interface 30, provided the professional staff has other confirmation of the existence of a valid prescription. If the validation of a prescription cannot be separately confirmed, the present invention system 10 provides for self-verification.

The controller 20 of the automated conveying system 12 is joined to a telecommunications modem 32. The telecommunications modem 32 communicates with a central office computer system 34 via a telecommunications link 36. The telecommunications link 36 can be a phone line, a broadband connection, a cellular connection or an internet connection.

The central office computer system 34 maintains a database 38. The database 38 contains information regarding various patients and the prescriptions outstanding for those patients. The database 38 is kept current via input from the physician's office that produced the prescription and/or the pharmacy that previously filled the prescription. In fact, the database 38 may be an existing database that is maintained by a pharmacy and is merely accessed by the central office computer system 34.

Figure 2:
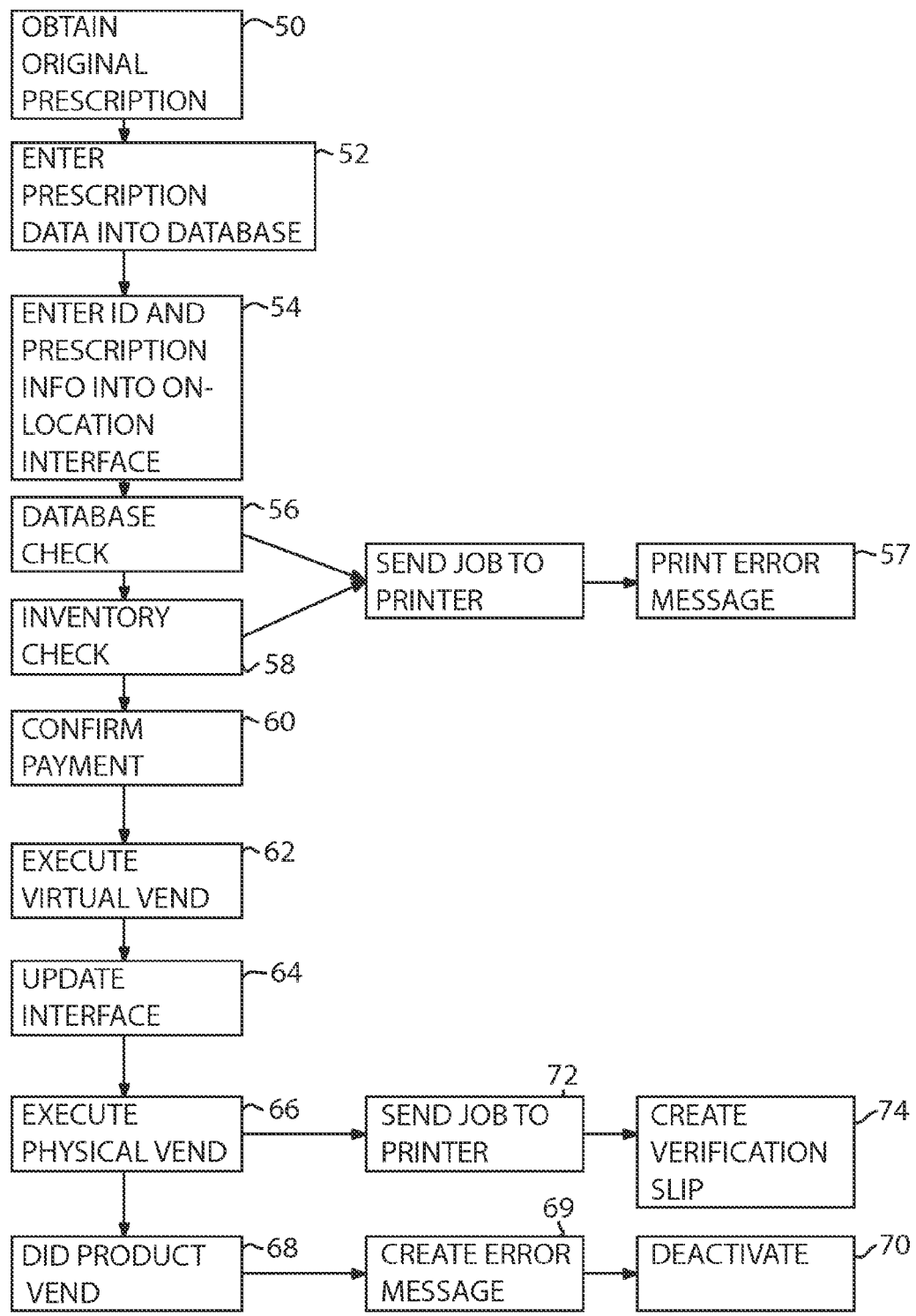
FIG. 2 is a block diagram showing the methodology used by the present invention system.

Having described an exemplary physical layout of the present invention system 10, the system's method of operation can now be described. Referring to FIG. 1 in conjunction with FIG. 2, it can be seen that the present invention system 10 is used to convey controlled materials, such as prescription pharmaceuticals. As is well known, a patient must first have a prescription from a physician before they are legally permitted to receive a prescription pharmaceutical. Accordingly, a patient must visit a physician and receive a prescription. See Block 50.

As is indicated by Block 52, once a prescription is received, the prescription data must be entered into the database 38 of the present invention system 10. This can be done by the professional staff at the physician's office. Alternatively, this can be done by the staff at a pharmacy when the prescription is first taken to be filled.

Once the prescription data is entered into the database 38, the patient can utilize the automated conveying machine 12. The automated conveying machine 12 can be used to provide the first unit-of-use 14 pursuant to the prescription. However, it is contemplated that the use of the automated conveying machine 12 is better adapted for use in providing refills of a prescription to a patient. If the automated conveying machine 12 is being used to supply refills, the prescription data and number of authorized refills is entered into the database 38 when the initial prescription is manually processed by a pharmacist.

To use the automated conveying machine 12, the patient's identification and requested unit-of-use 14 must be entered into the on-location interface 30. See Block 54. If the on-location interface 30 is accessible only by professional staff, the information is entered by the staff. If the on-location interface 30 is accessible to the public, the patient can enter his/her own information.

Once the controller 20 in the automated conveying machine 12 has received the input data regarding the patient requestor and the unit-of-use 14 being requested, a number of cross-reference checks are performed. As is indicated by Block 56, one of the cross-reference checks is checking the database to determine if the patient requestor is authorized to receive the unit-of-use 14 requested. In this cross-reference check, the existence of a valid prescription is checked as well as the time frame for renewals. For instance, a patient may only be entitled to one renewal every thirty days. Accordingly, a patient cannot request the refill if at least thirty days has not passed from the last filling of the prescription. If the database cross reference encounters a problem, the automated conveying machine 12 is not activated and an explanatory error message is printed for the patient. See Block 57.

In addition to the cross-reference check with the central database, a local inventory check is also performed. As is indicated by Block 58, the controller 20 in the automated conveying machine 12 knows what units-of-use 14 are contained within its inventory 16. If the patient requests a unit-of-use 14 that is not contained in the inventory 16, an explanatory error message is printed for the patient. See Block 57.

If a patient is authorized to receive a unit-of-use 14 and that unit-of-use 14 is present in the automated conveying machine 12, then the automated conveying machine 12 will convey the requested unit-of-use 14 upon confirmation of payment. See Block 60. As has been previously explained, confirmation of payment can be entered into the on-location interface 30 by the professional office staff. Alternatively, confirmation of payment can be generated by the patient directly using a payment device, such as a credit card reader located on the face of the automated conveying machine 12.

Once the automated conveying machine 12 has both database confirmation and payment confirmation, a virtual vend occurs in anticipation of a physical vend. See Block 62. During a virtual vend, the controller 20 deducts the selected unit-of-use 14 from the inventory 16 of the automated conveying machine 12, even though the automated conveying machine 12 has not yet physically yielded the unit-of-use 14. The controller 20 of the automated conveying machine 12 immediately updates inventory information, as is indicated by Block 64. In many scenarios, there may be a delay between the time a patient pays for a unit-of-use 14 and the time that the patient actually is present at the automated conveying machine 12. It will, therefore, be understood that once a patient has database confirmation and payment confirmation, the unit-of-use 14 in the automated conveying machine 12 is considered sold to that patient regardless to when, or if, the patient retrieves the unit-of-use 14 from the automated conveying machine 12. In this manner, if another patient is authorized to receive the same unit-of-use 14, the system will be able to tell if there is enough stock in the automated conveying machine 12 to meet the demand. A patient will, therefore, never arrive at the automated conveying machine 12 to find that a unit-of-use 14 that has been purchased is sold out. Another way of understanding this is to consider the system as having both a physical inventory and a virtual inventory. The physical inventory is inside the automated conveying machine 12. The virtual inventory is merely computer-controlled data. Initially, the physical inventory 16 and the virtual inventory match. The system will only work when a requested unit-of-use 14 is present both in the physical inventory and the virtual inventory. Once a person is confirmed to receive a unit-of-use 14, that unit of use is immediately removed from the virtual inventory. Once that person receives the unit-of-use 14 from the automated conveying machine 12, the unit-of-use 14 is removed from the physical inventory. The time delay between the virtual removal and the physical removal does not matter. However, by requiring that specific unit-ofuse be present in both the physical and virtual inventory prevents any one unit-of-use 14 from being sold more than once.

Once a patient has been database confirmed and payment confirmed, the automated conveying machine 12 is ready to physically dispense the prescribed unit-of-use 14. The automated conveying machine 12 moves a selected unit-of-use 14 from its inventory to its dispensing tray 24. See Block 66. Sensors 26 are located in the dispensing tray 24 of the automated conveying machine 12. The sensors 26 detect whether or not a selected unit-of-use 14 has been conveyed into the dispensing tray 24 after the automated conveying machine 12 has activated. See Block 68. If no prepackaged unit-of-use 14 is detected, it can be assumed that the prepackaged unit-of-use 14 got stuck or the automated conveying machine 12 was not filled properly and vended a blank space. If the controller 20 detects any such vending error, the controller 20 can alert the office staff and alert the operator of the automated conveying machine. See Block 69. The automated conveying machine 12 will also automatically deactivate to ensure that a subsequent patient does not receive the prepackaged unit-of-use 14 that may be only temporarily stuck within the automated conveying machine. See Block 70.

The printer 28 is connected to the controller 20 of the automated conveying machine 12. The printer 28 can be located within the automated conveying machine 12 or at some position close to the automated conveying machine 12. Every time the automated conveying machine 12 is activated by the controller 20, the controller 20 sends a print job to the printer. See Block 72. The print job corresponds to the unit-of-use 14 being conveyed. The printer 28 prints a verification slip 29 that contains information about the unit-of-use 14, such as its instructions for use and possible side effects. See Block 74. The verification slip 29 also contains identification information that helps ensure that the unit-of-use 14 that was vended was the unit-of-use that was intended.

Figure 3:
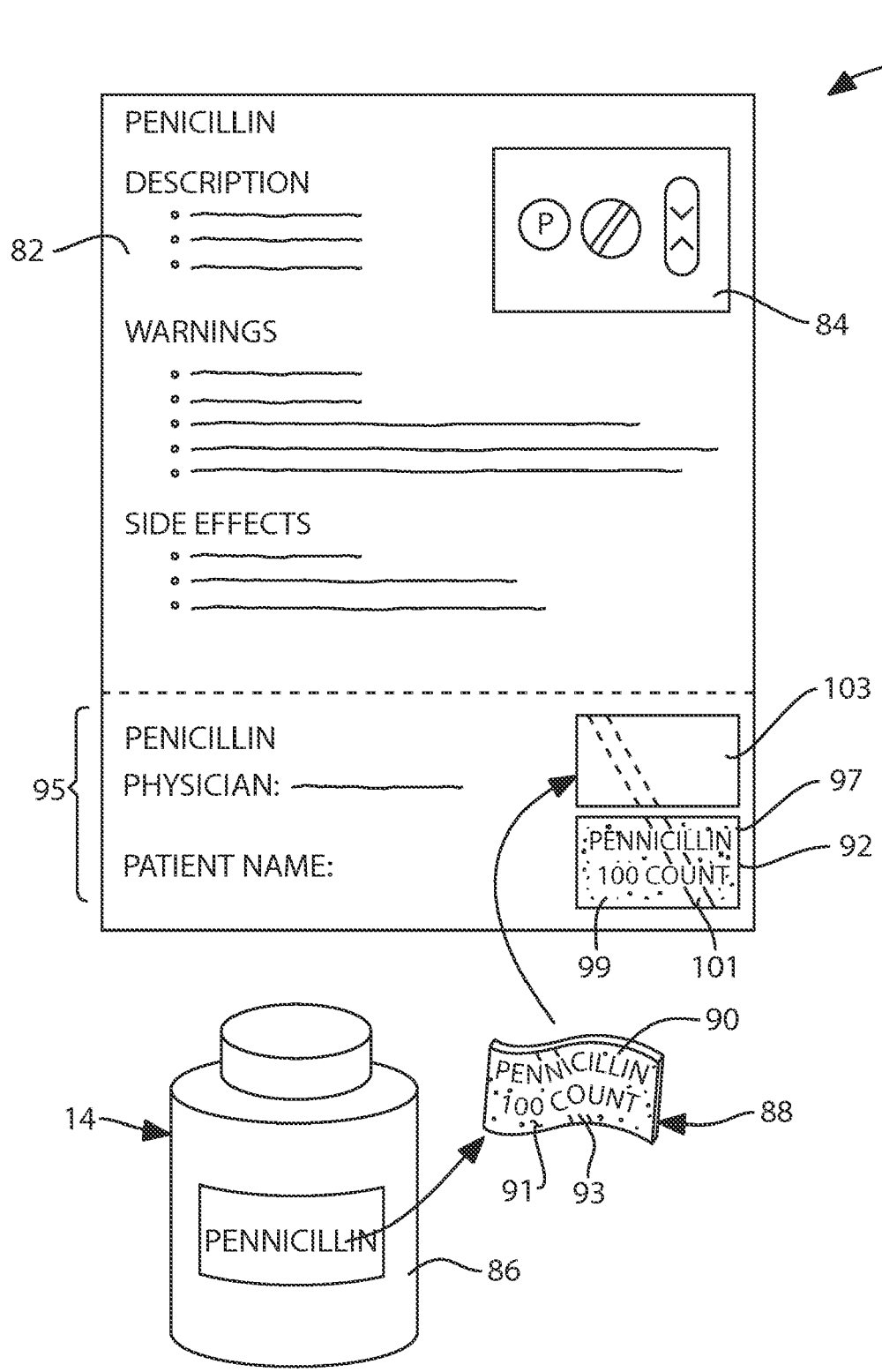
FIG. 3 shows an exemplary printout created by the present invention system and shown with a prepackaged pharmaceutical container.

Referring to FIG. 3, an exemplary embodiment of a verification slip 29 is shown. The verification slip 29 has an information section 82 that preferably contains some warnings and technical information about the pharmaceutical being conveyed. The verification slip 29 also has a picture section 84 that shows color pictures of the pharmaceutical being conveyed. More than one picture may be provided if the pharmaceutical is manufactured by more than one company and comes in different sizes, shapes and/or colors.

A unit-of-use in the form of a prepackaged pharmaceutical container 86 is also shown in FIG. 3. When such a prepackaged pharmaceutical container 86 vends from the automated conveying machine, it contains a removable label 88. The removable label 88 identifies the pharmaceutical that is in the prepackaged container 86 and also provides a code pattern 90 that is unique to that type of prepackaged unit-of-use. The code pattern 90 can be a color code, a numerical code, graphic code or any other visual code. In the exemplary embodiment, the code pattern consists of a color field 91 and an alignment strip 93.

The printout contains a tear-away section 95. A label image 92 is printed onto the tear-away section 95. The label image 92 contains a code pattern 97 that corresponds to the code pattern 90 on the removable label 88 from the prepackaged container 86. The label image 92 also contains a color field 99 and an alignment strip 101.

A label target 103 is printed either immediately above or below the label image 92. The label target 103 shows a person where to place the removable label 88 from the prepackaged container 86.

The removable label 88 is peeled off the prepackaged container 86 and is applied over the label target 103. Once in this position, the color field 91 of the removable label 88 should be the same color as the color field 99 of the label image 92. Furthermore, the alignment strip 93 of the removable label 88 should align with the alignment strip 101 on the label image 92.

By comparing the removable label 88 to the label image 92, two goals are achieved. First, by checking if the code patterns 90, 97 match, it can be seen that the proper prepackaged pharmaceutical container 86 was vended from the automated conveying machine 12. This safeguards against any human error that may have occurred during the filling of the automated conveying machine 12. Second, the tear-away section 95 of the printout is removed and kept by the office staff or patient, thereby providing a permanent record of what was vended from the automated conveying machine 12.

The automated conveying machine 12 is not an ordinary vending machine in the sense that it does not vend for money and it is not a self-contained system. Rather, the automated conveying machine 12 is used as the dispensing mechanism for a larger system that includes the central office computer system 34 and database 38.

Figure 4:
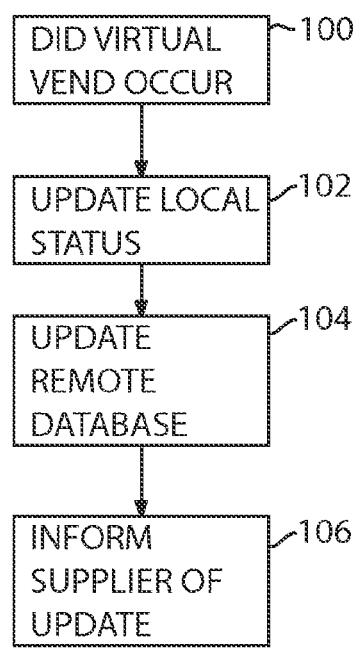
FIG. 4 is a block diagram showing yet another part of the methodology used by the present invention system.

Referring to FIG. 4 in conjunction with FIG. 1, it will be understood that as the automated conveying machine 12 vends, the controller 20 updates the status of the automated conveying machine 12. See Blocks 100 and 102. Information about what was vended and for whom is recorded in the database 38. See Block 104. In this manner, a patient's records are automatically updated with the prescription ordered by the physician and the medication that was conveyed.

As is indicated by Block 106, the controller 20 also forwards update information to the remote pharmacy source who is responsible for filling and maintaining the automated conveying machine 12. In this manner, the remote pharmacy source can periodically come to fill the automated conveying machine 12 before the automated conveying machine 12 ever runs out of a particular type of unit-of-use 14.

It will be understood that the embodiment of the present invention system that is illustrated and described is merely exemplary and that a person skilled in the art can make many variations to the system. Individual system parts, such as the key card, data input terminal, and data reading unit come in many different types. All variations of these components are intended to be included within the scope of the invention. Furthermore, the term automated conveying machine is being used in its broadest sense. The automated conveying machine is intended to include all storage devices, including locked storage chests, that can only be accessed upon the activation of some conveying mechanism. All such variations, modifications and alternate embodiments are intended to be included within the scope of the present invention as set forth by the claims.

What is claimed is:

1. A method of conveying regulated pharmaceuticals, comprising the steps of:
 providing a database that contains information on patients and prescriptions prescribed to said patients;
 providing an automated conveying machine having an inventory of prepackaged pharmaceuticals stored therein that can be independently vended upon the activation of said automated conveying machine, wherein each of said prepackaged pharmaceuticals contains a removable label with a first code pattern that is unique for a type of prepackaged pharmaceutical;

providing an interface proximate said automated conveying machine;

entering prescription data into said interface, said prescription data identifying a specific patient and a specific prepackaged pharmaceutical;

comparing said prescription data with information in said database for confirmation, wherein said automated conveying machine receives a confirmation signal if said prescription data is valid;

checking if a specific prepackaged pharmaceutical from said prepackaged pharmaceuticals is present within said inventory of said automated conveying machine;

activating said automated conveying machine if said specific prepackaged pharmaceutical is available in said inventory and said confirmation signal has been received;

providing a printer proximate said automated conveying machine, said printer printing a printout each time one of said prepackaged pharmaceuticals vends from said automated conveying machine, wherein said printout has a second code pattern thereon; and removing said removable label from said specific prepackaged pharmaceutical and placing said removable label onto said printout so that said first code pattern on said removable label lays in close proximity to said second code pattern on said printout.

2. The method according to claim 1, further including the step of electronically tracking said inventory of said prepackaged pharmaceuticals stored within said automated conveying machine.

3. The method according to claim 2, wherein said step of electronically tracking said inventory includes identifying if said specific prepackaged pharmaceutical is both physically present in said automated conveying machine and is available for vending.

4. The method according to claim 2, further including the step of indicating that a prepackaged pharmaceutical is available for vending only to said specific patient after said confirmation signal is received.

5. The method according to claim 1, further including the step of printing a printout if said confirmation signal is not received.

6. The method according to claim 1, further including the step of printing a printout if said prepackaged pharmaceutical is not in said inventory of said automated conveying machine.

7. The method according to claim 1, wherein each said printout contains a label image.

8. The method according to claim 1, wherein said step of providing a printer includes providing said printer within said automated conveying machine, wherein said printout extends from said automated conveying machine when printed.

9. The method according to claim 1, further including the step of sensing if one of said prepackaged pharmaceuticals vends from said automated conveying machine after said automated conveying machine is activated.

* * * * *